United States Patent [19]

Hagstrom et al.

[11] Patent Number: 5,366,898
[45] Date of Patent: Nov. 22, 1994

[54] METHOD FOR QUANTITATIVE DETERMINATION OF TOTAL BASE OR ACID NUMBER OF OIL

[75] Inventors: Richard A. Hagstrom, Cheshire; Stephen R. Finch, Durham; Timothy D. Lynn, Hamden, all of Conn.
[73] Assignee: Dexsil Corporation, Hamden, Conn.
[21] Appl. No.: 858,565
[22] Filed: Mar. 27, 1992
[51] Int. Cl.$^5$ ............... G01N 33/26; G01N 31/16
[52] U.S. Cl. ............................ 436/60; 436/61; 436/100; 436/101; 436/102; 422/58; 422/61; 422/75; 422/100; 422/101; 422/102; 604/241
[58] Field of Search .......... 422/58, 61, 75, 99, 422/100, 102, 101; 436/60, 61, 100, 101, 102; 604/241

[56] References Cited

U.S. PATENT DOCUMENTS

| | | | |
|---|---|---|---|
| 3,030,190 | 4/1962 | Seemann et al. | 23/230 |
| 3,193,356 | 7/1965 | Smith et al. | 23/230 |
| 3,259,463 | 7/1966 | Feasley et al. | 23/230 |
| 3,410,664 | 11/1968 | Fielding | 422/75 |
| 3,510,260 | 5/1970 | Krawetz et al. | 23/230 |
| 3,653,838 | 4/1972 | Glass | 23/230 HC |
| 3,653,839 | 4/1972 | Luks et al. | 23/230 R |
| 3,808,149 | 4/1974 | Ellis et al. | 252/408 |
| 3,811,837 | 5/1974 | Hoffman | 23/230 HC |
| 3,873,274 | 3/1975 | Neisius | 422/75 |
| 4,154,670 | 5/1979 | Forsberg | 208/180 |
| 4,203,725 | 5/1980 | Snowden, Jr. et al. | 23/230 HC |
| 4,238,197 | 12/1980 | Eisentraut et al. | 23/230 HC |
| 4,269,604 | 5/1981 | Snowden et al. | 23/230 HC |
| 4,405,448 | 9/1983 | Googin et al. | 208/262 |
| 4,430,208 | 2/1984 | Pytlewski et al. | 208/262 |
| 4,477,354 | 10/1984 | Fessler | 210/634 |
| 4,557,899 | 12/1985 | Schoonover et al. | 422/61 X |
| 4,686,192 | 8/1987 | Fisher | 436/60 |
| 4,731,332 | 3/1988 | Blumenthal et al. | 436/61 |
| 4,735,905 | 4/1988 | Parker | 436/174 |
| 4,873,056 | 10/1989 | Fisher | 422/61 |
| 4,925,627 | 5/1990 | Johnson | 422/99 |
| 4,962,039 | 10/1990 | Benedyk | 436/40 |
| 5,013,667 | 5/1991 | Lynn et al. | 436/126 |
| 5,028,543 | 7/1991 | Finch et al. | 436/124 |
| 5,055,410 | 10/1991 | Blumenthal et al. | 436/60 |

FOREIGN PATENT DOCUMENTS

| | | |
|---|---|---|
| 170466 | 2/1986 | European Pat. Off. . |
| 3401258 | 8/1984 | Germany . |
| 59-24384 | 6/1977 | Japan . |
| 54-49198 | 9/1977 | Japan . |

OTHER PUBLICATIONS

American Soc. for Testing and Mater., ASTM Designation D664–89, "Stnd. Test Meth. for Acid Number...", Jan. 1990.
American Soc. for Testing and Mater., ASTM Designation D2896–88, "Stnd. Test Meth. for Base Number...", Jan. 1989.
American Soc. for Testing and Mater., ASTM Designation D974–87 "Stnd. Test Meth. for Acid and Base Number...", Dec, 1987.
Barnes, "Importance of Railroad Diesel Oil TBN...", vol. 47, 9, 713–722 Lubrication Engineering.

*Primary Examiner*—Donald E. Czaja
*Assistant Examiner*—Milton I. Cano
*Attorney, Agent, or Firm*—Victor E. Libert; Frederick A. Spaeth

[57] ABSTRACT

The total base number of an oil sample of measured volume is determined by solvating the oil sample, adding a predetermined amount of acidic species to the solvated sample to react the acidic species with any basic species contained in the oil sample, extracting the remaining acidic species into an extractant phase, separating the extractant phase from the oil sample, and measuring the acidic species content of the extractant phase to determine the quantity of basic species in the oil sample. The same technique may be used to determine the total acid number of an oil sample by adding a predetermined amount of basic species to the sample and measuring the basic species content of the extractant phase. Apparatus comprising a test kit for carrying out the method comprises a sampling syringe (10) for drawing a fixed volume of sample oil, a reaction container (22) containing premeasured quantities of acidic species and solvent in first and second frangible ampules (28, 30) and a titration container (32) containing a pH indicator in a third frangible ampule (38). A titration syringe (50) contains a basic solution for titrating the extractant and bears graduations (55) which are scaled and numbered to indicate the total base number of the sample, and a cap (56) for securing the titration syringe (50) to titration container (32).

17 Claims, 2 Drawing Sheets

METHOD FOR QUANTITATIVE DETERMINATION OF TOTAL BASE OR ACID NUMBER OF OIL

BACKGROUND OF THE INVENTION

Field of the Invention

This invention relates to the testing for basic species present in oil, and more specifically to a method and apparatus for determining the total base number of a sample of oil.

Generally, additives such as anti-oxidants are often incorporated by the manufacturer into lubricating oils to extend the useful life of the oils. These additives are commonly alkaline, i.e., basic, chemical species (sometimes herein referred to as "basic species") which serve to alleviate the undesired effects of acidic species which may form under the operating conditions of the engine or other device lubricated by the oil. Over the course of extended use, the basic additives can be consumed or degraded, resulting in the build-up of acidic contaminants. Of course, lubricating oils which contain no or very little akaline additives are also subject to the build-up of acidic contaminants therein. The continued use of lubricating oil containing significant concentrations of such acidic contaminants can cause corrosive damage to the engine or other mechanism it is intended to lubricate. Accordingly, it is often desired to examine the condition of lubricating oil periodically to determine whether the oil is spent and needs replacement.

Gasoline, diesel oil and other liquid hydrocarbon fuels contain varying levels of sulfur or sulfur compounds, from negligible quantities to 5 percent by weight or higher. Accordingly, one of the products of combustion in the normal operation of, e.g., internal combustion engines powered by combusting such fuels, is sulfur dioxide which is usually exhausted from the cylinders in a gaseous state. However, when sulfur dioxide reacts with water vapor present in the combustion gases, it will form sulfurous acid which readily becomes oxidized to sulfuric acid, a corrosive by-product. Therefore, basic species additives such as calcium salicylate are often added to engine lubricating oils to combat the corrosive characteristics of sulfuric acid. The sulfur level in the fuel will usually determine the usable lifetime of the lubricating oil. That is, a high sulfur content of the fuel can destroy almost all of the base additives in relatively few hours of use. Consequently, tests for the total base number ("TBN") value of lubricating oils have been devised in order to assess the corrosiveness of the oil. Thus, in the case of oils which contain basic species additives, it is desired to measure the reserve alkalinity, i.e., to measure the quantity of the basic species additives in, or remaining in, the oil. For oils which are not formulated with or no longer contain basic species additives, it is desired to measure the quantity of corrosive acidic species contained in the oil to assess the amount of corrosives build-up. Consequently, tests for the total acid number ("TAN") value of lubricating oils have been devised in order to assess the corrosiveness of such oils. Usually, the TAN is of concern with respect to oils which are employed as lubricants in devices other than internal combustion engines. Accordingly, it is sound practice to periodically check the TBN of lubricating oils used in equipment, especially engines, such as the internal combustion engines of construction equipment, trucks, ships, etc., and to check the TAN of lubricating oils used in equipment other than internal combustion engines, such as compressors and gear boxes, to determine when the oil needs to be changed. The need for an oil change is indicated by a low TBN or a high TAN. The TBN is a number scale giving the quantity of acid, expressed in terms of mg of KOH equivalents per gram of oil sample; the TAN is a number scale giving the quantity of base, also expressed in terms of mg of KOH equivalents per gram of oil sample. In order to avoid damage to engines or other lubricated devices due to deterioration of the lubricating oil, it is highly preferable to be able to chemically determine the condition of the lubricating oil before degradation of the oil is visually evident. The alternative is the wasteful, and expensive, procedure of replacing lubricating oils at short intervals based on worst-case operation scenarios or placing the equipment at risk due to corrosion. The above discussion applies as well to oils used for purposes other than lubrication, so long as the corrosiveness of the oil is of concern.

Related Art

European Patent Publication 170,466, published Feb. 5, 1986, discloses a method and test kit for determining the alkalinity of oil. The method is colorimetric and is practiced by placing a fixed volume of an indicator solution comprising halogenated hydrocarbons in a titration container with a known amount of sample oil. The two are mixed together by shaking, and aqueous acid is added in fixed aliquots until a specific color change is brought about in the aqueous phase. The halogenated hydrocarbons in the indicator solutions make the density of the oil phase greater than that of water, so that the aqueous phase separates as the top layer.

U.S. Pat. No. 4,203,725 to Snowden, Jr. et al dated May 20, 1980, discloses a method and test kit for detecting the presence of contaminants in oil. This is accomplished by taking a sample of oil and adding a solvent-reagent. In the case of determining acidic or basic contaminants, the solvent is water (see column 8, lines 44-45) and the reagent is a pH indicator (see column 2, lines 48-56). The solvent-reagent solution is added to and mixed with the oil sample, and the mixture is allowed to separate. The color of the indicator in the lower, aqueous layer is observed and may be compared to a color scale to determine the contaminant content of the sample.

Several current Test Methods of the American Society for Testing and Materials ("ASTM"), Test Methods D2896-88, D974-87, D4739-87 and D664-89, disclose methods for the determination of TBN and TAN in petroleum products by forward and backward titrations with various acids. The D2896-88 procedure involves the use of a potentiometric titration system, the use of powerful and dangerous reagents including perchloric acid, glacial acetic acid, sodium perchlorate and chlorobenzene, and is designed to be carried out in a laboratory environment. The D664-89 procedure is a method for determining total acid number ("TAN") and the D4739-87 procedure is a TBN technique utilizing an electrode based titration. The D974-87 method uses less hazardous chemicals, but is a colorimetric test that cannot be used on dark colored oils which constitute the majority of used lubricating oils. More specifically, ASTM D974-87 discloses a titration method for determining the TBN or TAN of a sample of oil. Part 11 of this procedure, relating to a determination of strong acid number, teaches the taking of a fixed volume of sample, adding water, mixing the water with the oil sample, removing the water, adding an indicator (methyl orange) and titrating the water with a basic solution to determine the acid number. This test is limited to use with petroleum products which are soluble or nearly soluble in mixtures of toluene and isopropyl alcohol and is not suitable for measuring the basic constituents of many basic additive-type lubricating oils (see section 1.1, and note 2). This reference also teaches the determination of acid and base numbers by titrating a single phase comprising the sample and a "titration solvent" comprising toluene, isopropyl alcohol and about 5% water. See sections 9, 7.7, and 10.

U.S. Pat. No. 3,510,260 to Krawetz et al dated May 5, 1970, discloses a method for determining acid content of an oil sample comprising taking a sample of the oil and adding a pre-determined amount of base dissolved in an immiscible solvent (see column 2, lines 25-31). An oil diluent is also added, and the three components are mixed and allowed to separate. An indicator solution is added, and the color of the separated, immiscible layer is observed. This Patent teaches that the process may be reversed to test for basic species (see column 2, lines 44-52) and that by providing an immiscible layer in which to observe the color of the indicator, the difficulty of observing the color of darkened oil is avoided (see column 2, lines 53 through column 3, line 5 and column 3, lines 29-39).

A portable TBN test offered by Mobil Corporation is presently commercially available and involves the use of glacial acetic acid and petroleum distillates. It is designed to cover a limited TBN range and requires a predetermined estimate of the expected TBN value of the oil in order for the colorimetric endpoint to work effectively. Determination of the endpoint is difficult when dirty or contaminated oils are used and the instructional procedures recommend that a flashlight be used to determine the colorimetric endpoint. It is not designed to be operated or handled by relatively untrained persons. For obvious reasons of time and economy, it is desirable to be able to have relatively untrained persons field test the TBN of any lubricating oil at its point of use.

SUMMARY OF THE INVENTION

Generally, the present invention provides method and apparatus for testing the corrosiveness of oil by testing for either the total base number or total acid number, in either case by reacting the basic or acidic species being tested for with an acid, when testing for TBN, or with a base, when testing for TAN, and then back-titrating with a suitable titration liquid. The titration liquid is a base when testing for TBN and an acid when testing for TAN. The titration is carried out in a medium which is separated from the oil sample, and which preferably is removed from physical contact with the oil sample, to eliminate or reduce oil contamination of the titration medium.

Specifically, in accordance with the present invention there is provided a method for determining the quantity of a resident species (e.g., a basic species or an acidic species) present in a sample of oil. The method comprises the following steps. An oil sample of measured quantity is taken. Preferably, the oil sample is solvated in a quantity of organic solvent in which the oil sample and any resident species contained therein are soluble, to provide a solvent phase oil sample, so that the following steps which are carried out with the oil sample are preferably carried out with the solvent phase oil sample. In any case, whether solvated or not, the oil sample is contacted with a predetermined quantity of a reactant species. If the species in the oil, i.e., the resident species, is a basic species, then the reactant species is an acidic species. If the resident species is an acidic species, the reactant species is a basic species. In either case, the reactant species will react with the resident species, if any, present in the oil sample, thereby consuming a quantity of the reactant species commensurate with the quantity of resident species present in the oil sample. Thereafter, the oil sample is contacted with a fixed quantity of an extractant, preferably an aqueous extractant, but in any case one in which the reactant species is soluble but which is immiscible with the oil sample, in order to extract any unconsumed reactant species from the oil sample. The extractant is then separated from the oil sample, preferably including removing the extractant from contact with the oil sample, to thereby provide an extractant phase containing reactant species, if any, extracted from the oil sample. The reactant species content of the extractant phase is then measured to determine the quantity therein of unreacted reactant species as a measure of the resident species content of the oil sample.

In one aspect of the invention, the step of measuring the reactant species content of the extractant phase comprises adding a pH indicator to at least a portion of the extractant phase and titrating the extractant phase to the endpoint of the pH indicator using a titration syringe which contains a titration liquid which is basic when the resident species is basic and which is acidic when the resident species is acidic. The titration syringe may bear graduations which are scaled and numbered to directly indicate the total base number or the total acid number of the oil sample by the total amount of titration liquid expelled from the titration syringe into the extractant phase upon reaching the endpoint of the titration.

Another aspect of the present invention provides a method for determining the quantity of resident species present in a sample of oil wherein the resident species is selected from the group consisting of basic species and acidic species, in which the method comprises the following steps. An oil sample of measured quantity is taken and the oil sample is contacted with a quantity of organic solvent at least sufficient to dissolve therein the oil sample and the resident species, if any, present in the sample, to thereby provide a solvent phase. The solvent phase is then contacted with a predetermined quantity of a reactant species in an alcohol vehicle to react the reactant species with any resident species present in the solvent phase, thereby consuming a quantity of the reactant species commensurate with the quantity of resident species present in the oil sample. The reactant species is an acid (e.g., hydrochloric acid, nitric acid, sulfuric acid or perchloric acid) when the resident species is a basic species and a base (e.g., sodium hydroxide or potassium hydroxide) when the resident species is an acidic species. Thereafter, the solvent phase is contacted with an extractant in which the reactant species is soluble but which is immiscible with the solvent phase, to extract any unconsumed reactant species from the solvent phase. The extractant is then separated from the solvent phase, to thereby provide an extractant phase containing reactant species, if any, extracted from the solvent phase. The reactant species content of the extractant phase is then measured to determine the quantity therein of unreacted reactant species as a measure of the resident species content of the oil sample.

In accordance with an apparatus aspect of the present invention there is provided an improvement in an apparatus for determining the quantity of resident species present in an oil sample. The improved apparatus comprises sampling means for drawing a measured quantity of an oil sample and introducing the measured sample into a container system, and a container system comprising at least a first container having a closable mouth dimensioned and configured to receive materials therethrough and containing therein a measured quantity of one or more reactants. The improvement comprises the provision of a titration burette in the form of a syringe containing a titration liquid, and dimensioned and configured to expel the titration liquid in a controlled stream therefrom and having graduations thereon to indicate the total amount of titration liquid expelled from it. The syringe also has a spout through which the titration liquid is expelled, and a cap member dimensioned and configured to close and seal the first container and position the spout for introduction of titration liquid into the sealed container. In this way, the contents of the first container are sealed against entry into or removal therefrom of any ingredients save titration liquid emitted by the titration syringe, and the sealed first container with the titration syringe attached thereto may be shaken simultaneously with introduction of titration liquid therein without loss or contamination of the contents of the first container.

In one aspect of the invention, the apparatus is dimensioned and configured to determine the amount of basic species contained in an oil sample, and the graduations on the syringe comprise a scale of total base numbers. In another aspect, the apparatus is dimensioned and configured to determine the amount of acidic species contained in an oil sample, and the graduations on the syringe comprise a scale of total acid numbers.

In yet another aspect of the present invention, the container system further comprises a second container, the first and second containers each having a mouth dimensioned and configured to receive materials therein. In this aspect, the second container further comprises a second cap member dimensioned and configured to selectively open and close the mouth of the second container, and at least one of the reactants contained in the first container and at least one of the reactants contained in the second container are contained within respective frangible ampules in the containers. The first and second containers are sufficiently resilient to enable crushing of the frangible ampules contained therein to release their contents within the respective containers by squeezing the containers from the exterior thereof.

Yet another aspect of the present invention provides for an apparatus dimensioned and configured to determine the amount of basic species contained in an oil sample, wherein the second container comprises a reaction container having disposed therein a first frangible ampule containing an organic solvent for dissolving the oil sample to provide a solvent phase, and a second frangible ampule containing an acidic species, e.g., one selected from the group consisting of hydrochloric acid, nitric acid, sulfuric acid and perchloric acid, in an alcohol vehicle. The first container comprises a titration container containing an extractant which is immiscible with the solvent phase but in which the reactant species is soluble, and a third frangible ampule containing a pH indicator.

As used herein and in the claims, "basic species" and "acidic species" have the following meanings. The term "basic species" is used to broadly mean not only strong bases but to include other compounds or substances which are suitable for use as additives in lubricating and other oils and capable of reacting with or otherwise neutralizing the corrosive effect of acids and acidic species which accumulate in or otherwise are contained in such lubricating and other oils. The term "acidic species" is used to broadly mean not only strong acids but to include other compounds or substances which exhibit corrosive properties in lubricating or other oils and which are neutralizable by basic species so as to eliminate or ameliorate their corrosive properties.

BRIEF DESCRIPTION OF THE DRAWINGS

FIGS. 1-5A collectively show the components of one embodiment of a test kit according to the present invention, each component being shown in an elevation view, save for FIG. 4, wherein:

DETAILED DESCRIPTION OF THE INVENTION AND SPECIFIC EMBODIMENTS THEREOF

The present invention provides a method and apparatus for evaluating the total base number ("TBN") or the total acid number ("TAN") of a sample of oil, such as a used lubricating oil. Generally, the methods and techniques of the present invention are substantially identical with respect both to testing for TBN and TAN except that, naturally, different reactants, titration liquids, etc., are employed. For economy of expression, the bulk of the following discussion will be related to those embodiments of the invention which pertain to the determination of TBN, although it will be appreciated that the same principles apply to methods and apparatus for the determination of TAN.

Figure 1:
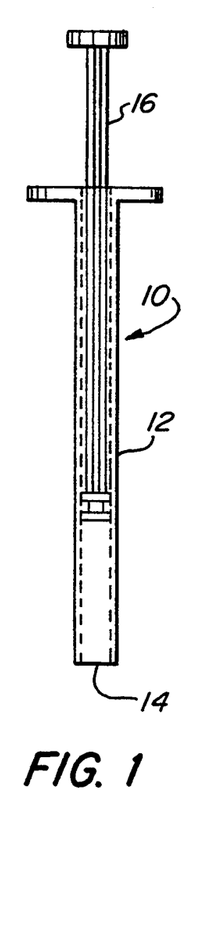
FIG. 1 shows a sampling syringe.

The sample of oil to be tested may be taken in any convenient manner, for example, by drawing some oil from an engine crankcase into a suitable container such as a cup or can, and then using a suitable device, such as the sampling syringe illustrated in FIG. 1, to draw a measured quantity of the oil. Many lubricating oils contain corrosion inhibitors and oxidation inhibitors which will react with a strong acid such as hydrochloric acid and thus constitute "basic species" as that term is used herein and in the claims. Typical corrosion inhibitors are zinc and other dithiophosphates, metal sulfonates, overbased metal sulfonates, metal phenate sulfides, overbased metal phenate sulfides, acid phosphate esters, etc. Oxidation inhibitors include zinc dithiophosphates, metal dithiocarbamates, hindered phenols, phenol sulfides, metal phenol sulfides, metal salicylates, aromatic amines, dilauryl selenide, etc.

The measured sample of oil is contacted with a predetermined amount of a suitable acid, sometimes here and in the claims referred to as an "acidic species". If a "basic species" such as the alkaline additives added by oil manufacturers to lubricating oils are present in the oil, they react with and consume some or all of the acidic species added to the sample.

Preferably, the oil sample is first mixed with a solvent in which the oil sample and the basic species, if any, contained therein are soluble, to provide a solvent phase in which the oil and basic species are dissolved, and to which the predetermined amount of acidic species reagent is added. The solvent may be, e.g., isooctane, and the solvent phase provides a reaction medium which enhances the reaction of the basic species components of the oil sample with the acidic species reagent added in the test and facilitates clean extraction of acidic species from the solvated, reacted oil sample. The acidic species reagent may be an alcoholic acid solution, that is a strong acid such as hydrochloric acid in an alcohol vehicle, such as an isopropyl alcohol vehicle. The use of a solvated oil sample also facilitates subsequent phase separation of the oil residue and an extractant, e.g., an aqueous extractant, as discussed below.

The acidic species which remains after the reaction of the acidic species reagent, e.g., a solution of a strong acid, such as HCL in an alcoholic vehicle, with the basic species present in the oil sample is then extracted into a liquid extractant in which the acidic species is soluble but which is immiscible with the oil or, when a solvent is used to provide a solvent phase, which is immiscible with the resulting solvent phase. Preferably, the extractant is an aqueous extractant which can be mixed with the oil sample or with the solvent phase, i.e., the solvated oil sample, and which thereafter separates from the mixture to form a distinct layer of an extractant aqueous phase. A clean phase separation of the solvated hydrocarbon residue and the aqueous phase having the resultant acid dissolved therein enables a more complete recovery of the resultant acid and the concomitantly greater accuracy in determining the total base number of the oil sample. However, a suitable non-aqueous extractant may be used, provided that the acidic species reagent is soluble in the extractant, and that the extractant is immiscible in the oil sample or, when a solvent is used, in the resulting solvent phase.

The quantity of acidic species which survives the reaction with the basic species and therefore is available for extraction into the extractant phase will be determined by the quantity of basic species in the oil sample tested. Therefore, the acid level of the extractant phase is indicative of the quantity of basic species remaining in the oil sample.

A pH indicator is added to the extractant phase to give a visual indication of the endpoint of the titration. Alternatively, a pH meter or any other suitable instrument or technique to determine the acid content of the extractant phase could be employed. A pH meter is perhaps more appropriate for use in a laboratory environment whereas a liquid titration provides a technique which is better suited for use in a field test kit, as titration and the color-change endpoint is simpler for untrained personnel to use. Preferably, after a fixed quantity of the extractant is thoroughly mixed with the oil sample or the solvent phase oil sample, a specific, measured quantity of the extractant phase is drawn into a separate container, and the pH indicator is added to the premeasured quantity of withdrawn extractant phase. The acid content of the extractant phase is then determined by any suitable means. A convenient means, especially for a field test kit, is titration, for example, by using a titration syringe which contains a basic titration liquid and has suitable graduations marked thereon. The basic titration liquid, the predetermined amounts of acidic species and of extractant, the endpoint of the pH indicator and the graduations on the syringe are all selected so that the total amount of basic titration liquid expelled from the syringe in order to reach the endpoint of titration of the premeasured quantity of the extractant phase may be directly read as the total base number of the oil sample tested. Obviously, any suitable graduations may be used. For example, volume graduations may be used and a suitable conversion chart may be provided which relates the volume of titration liquid expelled to the total base number or, in the case of an apparatus designed to determine the acidic species content of an oil sample, to the total acid number. In the case of determining the basic species content of an oil sample, the titration liquid may be an aqueous solution of a strong base, e.g., sodium hydroxide or potassium hydroxide.

In addition, the syringe may incorporate a cap member dimensioned and configured to serve as a closure for the container in which the titration is performed. When the cap member of the titration syringe is in place as a closure on the titration container, the spout of the syringe is disposed within the interior of the container so that the contents of the syringe may then be added to the extractant phase to perform the titration. The cap member of the titration syringe and the titration container are so dimensioned and configured that the cap member closes and seals the titration container, positions the spout for introduction of titration liquid into the titration container, and seals the titration container so that nothing (except titration liquid) can enter and nothing can be spilled therefrom. This permits shaking of the titration container while injecting titration liquid therein in order to enhance the accuracy of the titration step.

A method for determining the base number of a sample of oil is thus carried out by adding a known quantity of acidic species to react with the basic species in the oil, extracting the acidic species which survive the reaction into an extractant in which the acidic species is soluble but which is immiscible with the oil sample (or with a solvated oil sample), and adding a pH indicator to at least a portion of the extractant to enable visual determination of the endpoint of the titration of the extractant phase. By allowing the user to observe the pH indicator and titration endpoint in an extractant phase which is separated from the oil sample, observation of the pH indicator is made possible, or at least facilitated, because the oil sample, which is usually quite dark and opaque in the case of a used lubricating oil or the like, does not obscure the color and color change of the pH indicator. The measured quantity of added titration liquid indicates the quantity of surviving acidic species from the known quantity added to the premeasured oil sample, and therefore the quantity of basic species present in the oil sample tested.

The present invention provides an apparatus in which the reagents necessary to carry out this process are conveniently premeasured and stored so that the user may release the reagents and carry out the titration without jeopardizing the accuracy of the test due to spillage, measuring errors and the like. Use of a titration syringe bearing graduations which are scaled and numbered to directly indicate the total base number of the sample at the endpoint of the titration obviates the need for the user to perform any computations to interpret the results of the test. The apparatus is therefore readily usable by persons unskilled in laboratory analysis techniques and may be used in the field by untrained persons by simply following relatively simple (as compared to laboratory analyses) instructions.

Although the method of invention may be carried out by any suitable apparatus, including laboratory apparatus, one of its significant advantages is that it may be accurately carried out in a field test kit and moreover, in a field test kit which is sufficiently inexpensive that it is economically feasible to use the kit once and then discard it. A suitable field test kit for carrying out the method of the invention conveniently employs prepacked, premeasured reagents in accurately measured quantities, thereby facilitating the use of the test kit by inexperienced personnel with very little or no prior training.

In a specific embodiment, a test kit according to the present invention includes a sampling syringe 10 (FIG. 1) having a cylinder portion 12, a spout portion 14 and a plunger 16. Plunger 16 and cylinder portion 12 are dimensioned and configured so that a sample drawn by the full travel of plunger 16 within cylinder portion 12 provides a precisely measured sample of known volume, e.g., 0.37 ml. Once the sampling syringe 10 is filled with an oil sample, suction sufficient to hold the oil sample in place within the syringe is maintained simply by leaving the plunger undisturbed in place. The kit further includes a resilient reaction container 22 (FIG. 2) of generally test tube shape into which the oil sample taken is deposited. Reaction container 22 contains the solvent (e.g., 1.0 ml of isooctane) in a first frangible ampule 28 and a predetermined amount of an alcoholic acid (e.g., 1.0 ml of 0.114N HCl in isopropyl alcohol) in a second frangible ampule 30. The hydrochloric acid content of second ampule 30 provides an acidic species to react with basic species provided by the usual alkaline additives in, or remaining in, the oil sample, if any. Both ampules 28 and 30 in reaction container 22 are supported by ampule holder 26 comprising a stiff but flexible split tube within which ampules 28 and 30, which are of a diameter somewhat greater than the inside diameter of the split tube, are retained by the gripping pressure of the split tube. Ampule holder 26 is supported by a leg portion 26a thereof which is seated at the bottom end of reaction container 22. Reaction container 22 is sufficiently resilient so that the user may crush frangible ampules 28 and 30 to release the contents thereof by squeezing the outside of reaction container 22. Reaction container 22 is made of any suitable resilient material which is sufficiently transparent to permit visual observation of the contents of reaction container 22, to observe mixing and separation of the reactants, etc., as described below. Screw threads 22b are formed adjacent to and extending from the mouth 22a of reaction container 22 so as to enable container 22 to threadably receive a screw-on cap 24. Cap 24, which serves to close container 22, is removable and replaceable on container 22 and is fitted with a valve spout 24a having a spout conduit 24b extending therethrough, and has a cap conduit 24c formed therein. Valve spout 24a is pivotably mounted within cap 24 so that it is pivotable, as indicated by the unnumbered arrow in FIG. 2, between a closed position shown in solid line rendition in FIG. 2 and an open position shown in phantom outline in FIG. 2. In the closed position illustrated in FIG. 2, spout conduit 24b is out of alignment with cap conduit 24c and seated against an interior wall (not numbered) of cap 24 whereby spout conduit 24b is sealed against flow therethrough. In the closed position illustrated, valve spout 24a is flush with the flat top 24d of cap 24. In the open position shown in phantom outline in FIG. 2, valve spout 24a is disposed at right angles to top 24d of cap 24 and spout conduit 24b is in alignment with cap conduit 24c which extends through hemispherical base portion 25 of cap 24 to allow fluid flow from the interior of container 22 through cap 24.

Figure 2:
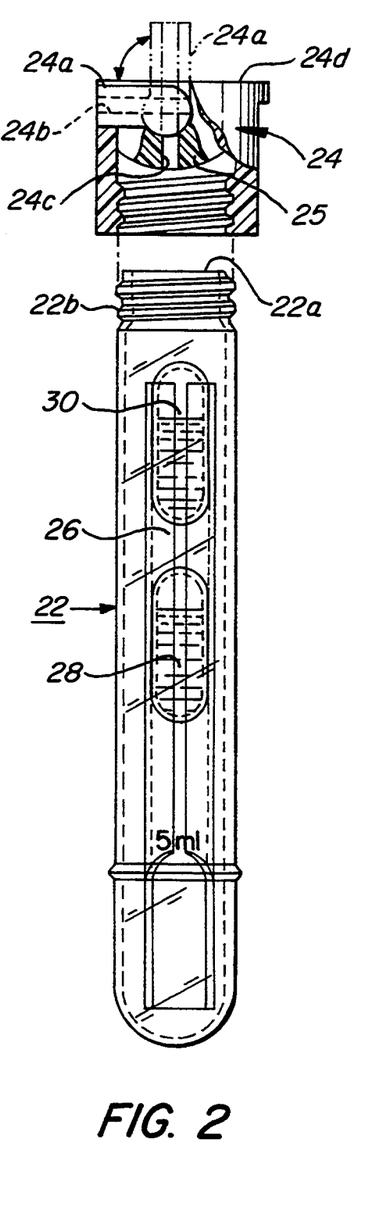
FIG. 2 shows, in partial cross section, a flexible reaction container containing two frangible ampules containing, respectively, a solvent and an alcoholic acid, and having a sealable spout.

In use, a measured sample of the oil to be tested is taken, for example by drawing a quantity of oil from an engine crankcase and thoroughly mixing the sample. Sampling syringe 10 is then inserted into the thoroughly mixed oil sample and plunger 16 thereof is drawn fully back to fill sampling syringe 10, taking care that no air bubbles are formed within the syringe. Alternatively, the oil sample quantity may be taken by weighing the oil sample. However, a volumetric sampling technique is simpler to carry out, especially in a field test kit designed for use by relatively untrained persons. If there are air bubbles, the sample is expelled and a fresh sample taken to completely fill the syringe so that a measured quantity of oil sample is obtained. The exterior of the syringe tip inserted into the oil is then wiped clean to remove therefrom excess oil which might otherwise get into container 22 and thereby increase the size of the sample introduced into container 22 beyond the premeasured quantity contained within the cylinder portion 12 of syringe 10. The user removes cap 24 from reaction container 22 and deposits the sample oil from sampling syringe 10 into reaction container 22 by positioning spout 14 of syringe 10 in the mouth 22a of reaction container 22 and depressing plunger 16 to expel the entire measured oil sample from syringe 10 into the reaction container 22. The user then discards syringe 10 and replaces cap 24 with valve spout 24a in the closed position.

While it is possible to add the acidic species reagent directly to the sample oil, it is preferable to first solvate the sample oil by adding a solvent in which the oil sample and the basic species contained therein are soluble. The solvent dissolves the oil sample to produce a solvent phase oil sample (sometimes herein referred to simply as a "solvent phase") having a lower viscosity than the oil sample. The lower viscosity, together with the use of an acidic species of enhanced miscibility (relative to an aqueous acidic species) with the oil sample solvent phase, e.g., HCl in isopropyl alcohol, facilitates completion of the reaction between any basic species in, or remaining in, the oil sample and the added acidic species reagent.

To add the solvent to the measured oil sample, the user squeezes container 22 to crush first frangible ampule 28, thus releasing the premeasured quantity of isooctane solvent into container 22. The sample oil and solvent are mixed together by shaking the container to provide a solvent phase oil sample. The user then squeezes container 22 to crush second frangible ampule 30, thus releasing the premeasured quantity of alcoholic acid (HCl in isopropyl alcohol) and again shakes the container 22 to thoroughly mix the contents. Some or all of the acidic species, i.e., the HCl, reacts with and is mutually consumed by the basic species, if any, present in the oil. By providing the acidic species in an alcohol vehicle, the miscibility of the acid with the oil sample, or with the solvated oil sample, is enhanced as compared to an aqueous acid solution. The enhanced miscibility of the acidic species facilitates the degree of completion of the reaction between the basic species, if any, contained in or remaining in the oil sample to be tested, and the acidic species introduced in the test. Generally, alcohols having carbon chains of at least three carbon atoms, i.e., $C_3$ or higher alcohols, are preferred because of their greater miscibility with oil than that of $C_1$ or $C_2$ alcohols.

As to the choice of acid to be used as the acidic species to react with the basic species present in the oil, the strength of the acid, i.e., its ability to react with and neutralize basic species contained in the oil, will of course effect the TBN determined by the test. Those skilled in the art will appreciate that this factor, the strength of the acid utilized, must be taken into account in assessing the meaning of the TBN number obtained. Conventionally, a strong acid such as hydrochloric acid or perchloric acid is utilized in the test to provide generally accepted TBN values for lubricating oils. However, other acids may be used, including sulfuric acid or nitric acid.

The kit further contains a resilient titration container 32 (FIG. 3) which includes a measured quantity of liquid extractant 42 in which the acidic species is soluble but which is immiscible with the oil sample, whether the oil sample is solvated or not. The amount of extractant provided is greater than that required to carry out the titration portion of the test, for reasons described below. Titration container 32 contains a pH indicator in a third frangible ampule 38, which is supported by an ampule holder 36 similar to ampule holder 26 in reaction container 22. The indicator, which may comprise 200 microliters of conventional methyl red solution, is released into the extractant phase by crushing third ampule 38 by squeezing resilient titration container 32 from the outside. Like reaction container 22, titration container 32 is of generally test tube shape and is made of material which is sufficiently resilient to recover its shape after being squeezed sufficiently to crush the frangible ampule contained therein, and sufficiently transparent to permit the user to observe conditions and colors within the containers. Containers 22 and 32 may, as noted above, be made of any suitable resilient material, e.g., polyethylene, and may be identical to eliminate the need to stock and provide two different types of container, even though a volume-indicating mark (described below) required on container 32 is not needed, but is not inconvenient, on container 22. The caps 24 and 33 used on, respectively, containers 22 and 32 may be differently colored to facilitate following instructions which may form part of the test kit.

Figure 3:
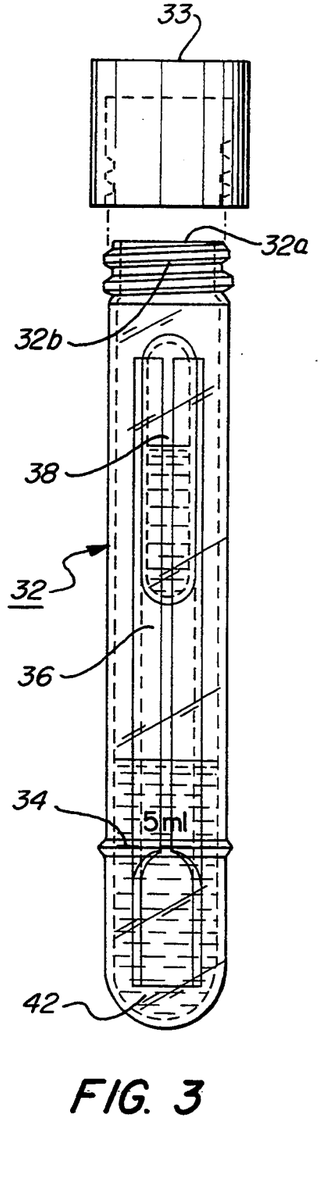
FIG. 3 shows a flexible titration container having a fixed volume indicator and containing two frangible ampules containing, respectively, an extractant and a pH indicator.

Titration container 32, like reaction container 22, has threads 32b formed adjacent to its mouth 32a so that container 32 can be sealed by a screw-on cap 33, thus sealing liquid extractant 42 inside titration container 32 until the user is ready to pour the extractant 42 into reaction container 22. Preferably, the extractant 42 is an aqueous solution which may contain an emulsion-breaker, e.g., 7 ml of 1 % $Na_2SO_4$ in water, to provide a solution in which the acidic species is soluble and is immiscible with the oil sample or the solvated oil sample. The sodium sulfate serves to inhibit the tendency of any surfactants which may be in the oil sample to lead to the formation of an oil-extractant emulsion. Caps 24 and 33 are removed from, respectively, containers 22 and 32 and the premeasured quantity of extractant is poured from titration container 32 into reaction container 22 containing the solvated oil sample, taking care not to permit ampule holder 36 to spill out of titration container 32. Cap 24 is then replaced on container 22 with valve spout 24a closed so that the contents of container 22 can be vigorously mixed by shaking container 22. After shaking, the container 22 is vented by unscrewing and then retightening cap 24. Cap 33 may be replaced on titration container 32 to preclude contamination. Any acidic species not consumed by reaction with the basic species present in the oil sample are thus extracted into the aqueous extractant layer. Container 22 is then inverted with valve spout 24a still in the closed position, and the immiscible extractant is allowed to separate from the oil, the extractant phase forming as a bottom layer immediately adjacent to cap 24 and the solvated oil, being less dense than the extractant phase, rising to a top layer within reaction container 22. The flat configuration of top 24d enables the user to place reaction container 22 with surface 24d resting on any convenient flat surface where container 22 is left undisturbed to allow the mixture therein to separate into the separate aqueous extractant and solvent phase layers. The emulsion-breaker provides a faster separation of the aqueous and solvent phase layers; phase separation is typically achieved in about three minutes. The solvated oil phase, being of lower density than the extractant phase, remains as a separated layer floating on, i.e., above, the extractant phase.

Figure 4:
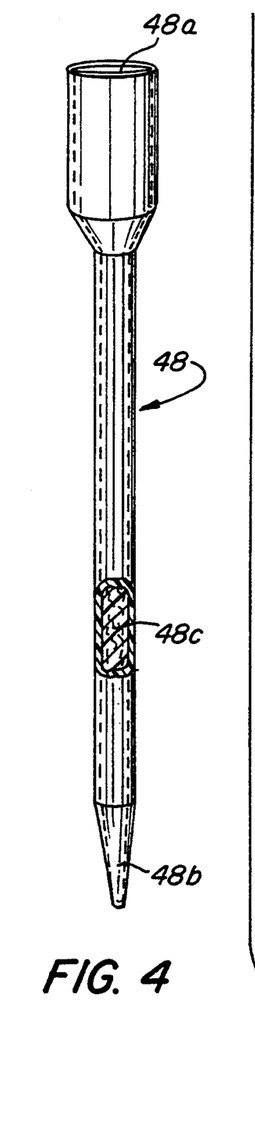
FIG. 4 is a perspective view of a filtering funnel.

After the two phases have separated into distinct layers, a fixed quantity of the acid-containing extractant is introduced from reaction container 22 into titration container 32 through a filter funnel 48 (FIG. 4). This is accomplished by removing cap 33 from titration container 32 and inserting funnel spout 48b of filter funnel 48 into the mouth of titration container 32, and introducing extractant from reaction container 22. Reaction container 22 is picked up gently, to avoid re-mixing the separated phases, and while being kept inverted, i.e., with cap 24 facing downwardly, gently opening valve spout 24a and delivering a stream of the extractant layer into funnel mouth 48a by gently squeezing the exterior of container 22, to force extractant phase through conduits 24c and 24b of cap 24, thence through filter funnel 48 and into titration container 32, to the volume indicator provided by rib 34 which, in the illustrated embodiment (FIG. 3), indicates a volume of 5 ml. If it is necessary to squeeze the container 22 more than once in order to dispense the necessary amount of extractant phase, the container 22 is gently and slowly released between squeezes so that the solvated oil and extracted layers are not mixed by re-entering air. Container 22 may be discarded at this point. The extractant is seen to be physically separated from the solvated oil phase promptly upon phase separation being attained. This eliminates absorption into the extractant of oil or components of the oil sample which might interfere with the accuracy of the titration, as might occur if the separated solvated oil and extractant layers were separated into phases but the phases were allowed to remain in contact with each other at the phase boundary. As an added precaution a filter is used, filter funnel 48 containing a filter material such as a polypropylene felt plug 48c to trap any minute quantities of organic contaminants such as oil, which may be suspended in the extractant phase.

As noted above, the amount of extractant provided is greater than that which must be transferred to titration container 32. This enables leaving behind within reaction container 22 enough extractant phase to keep the oil phase floating above and out of contact with cap 24 while reaction container 22 is inverted, thereby preventing the passage of any of the solvated oil sample into titration container 32. The titration is thus carried out in an environment which is physically separate from the oil sample. When the measured amount of extractant phase is delivered into titration container 32, cap 33 is then replaced on container 32 and the measured amount of pH indicator is then released into the measured quantity of extractant phase contained in container 32 by squeezing container 32 from the outside to crush third frangible ampule 38 which contains the pH indicator, and shaking titration container 32 to mix the pH indicator with the measured amount of extractant phase.

Once the pH indicator has been added to the fixed amount of extractant in titration container 32, which is an environment free of the usually opaque oil sample being tested, the user may readily observe the condition of the indicator to determine the pH level of the extractant and thus determine the quantity of basic species present in the oil sample tested. This observation is advantageously accomplished by titration, so that the total base number of the sample oil can be quantitatively determined. For this purpose, the test kit includes a titration syringe 50 (FIG. 5) which contains a titration liquid, in this case an aqueous solution of a basic species, such as an aqueous solution of a strong base, e.g., NaOH or KOH. The titration liquid is added to the extractant until the pH indicator reaches its endpoint. The quantity of basic solution thus delivered to the extractant is indicative of the total base number of the oil sample tested.

Figure 5:
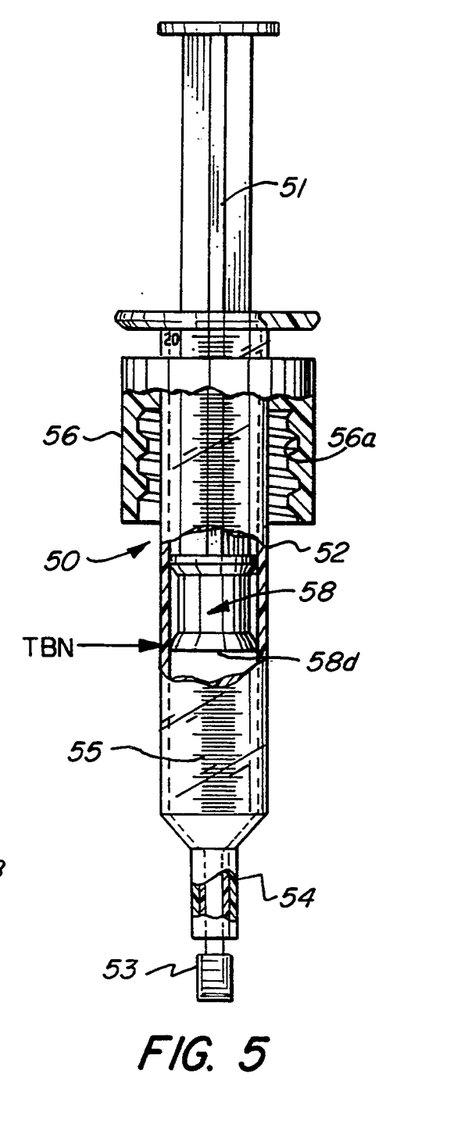
FIG. 5 shows, in partial cross section, a titration syringe (including the plunger of FIG. 5A assembled thereto) dimensioned and configured to be secured to the titration container of FIG. 3.
Figure 5A:
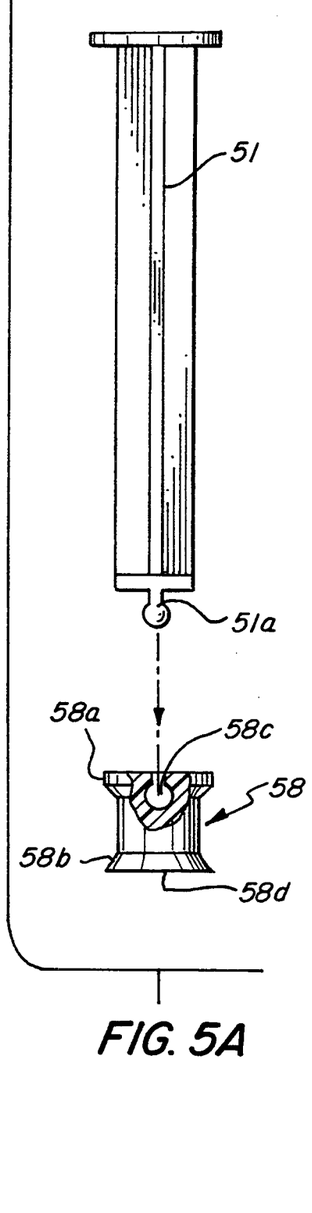
FIG. 5A shows a plunger for use as part of the titration syringe of FIG. 5 and, in partial cross section, an exploded view of the plunger head shown in FIG. 5 and forming part of the titration syringe of FIG. 5.

In the illustrated embodiment, titration syringe 50 contains an aqueous solution of sodium hydroxide, for example, 1 ml of 0.064N NaOH, as the titration liquid. Titration syringe 50 is advantageously made from a molded plastic material and generally comprises a conventional cylindrical body 52 having a discharge spout 54 which is closed by a break-away closure tip 53 which closes off the discharge spout 54. A plunger head 58 is slidably received within body 52 at the end of body 52 furthest removed from discharge spout 54. Plunger head 58 is snugly received within body 52 and has sealing collars 58a and 58b which provide a liquid-tight seal within body 52 so that a titration liquid is sealed within body 52, between plunger head 58 and closure tip 53. The plunger 51 (FIG. 5A) of the titration syringe is conveniently provided separately, that is, not mounted in the plunger head 58. This shortens the length of titration syringe 50 for packaging and shipment.

Threaded syringe cap 56 is slidably mounted on the body 52 of titration syringe 50. Threads 56a of cap 56 are dimensioned and configured to be threadably received on the threads 32b of titration container 32, so that syringe 50 may be mounted upon container 32 with discharge spout 54 thereof positioned within titration container 32. The diameter of ampule holder 36 is small enough relative to the inside diameter of titration container 32 that ampule holder 36 would not impede the insertion of the body 52 of syringe 50 within titration container 32.

Plunger rod 51 is sized to be received within body 52 of titration syringe 50 and has an insertion tip 51a (FIG. 5A) which is dimensioned and configured to be snap-fitted within cavity 58c of plunger head 58. Titration syringe 50 has applied thereto graduations 55 which are scaled and numbered to directly correspond to the total base number of a tested oil sample as indicated by the volume of titration liquid (in this case a basic solution, e.g., an aqueous solution of NaOH) required to titrate the extractant to the indicator endpoint. In the case of the specific reagents exemplified in the foregoing description, the endpoint is seen as a change in color from magenta to yellow. Therefore, when the user employs titration syringe 50 to titrate the extractant phase to the endpoint of the pH indicator, the number of the graduation at which plunger 51 comes to rest gives the total base number of the oil sample. This obviates the need for the user to perform any calculations to determine the total base number of the sample. Alternatively, the kit may comprise a color chart giving the pH and/or the total base number of the sample when the pH indicator attains a particular color shade. This latter technique is somewhat subjective and generally not as accurate as the use of graduations on the titration syringe. Generally, the use of a titration liquid as opposed to premeasured quantities of titer enables use of infinitely small increments of titer and a correspondingly more accurate test.

In the illustrated embodiment, the numbered graduations on the titration syringe indicate 0.5 milliliter ("ml") increments of the basic solution in the syringe. Unnumbered lines indicate equal volume increments between the numbered graduations. The direct reading TBN scale 55 is as follows:

| ml of Basic Titration Solution | TBN |
| --- | --- |
| 0.0 | 20 |
| 0.1 | 18 |
| 0.2 | 16 |
| 0.3 | 14 |
| 0.4 | 12 |
| 0.5 | 10 |
| 0.6 | 8 |
| 0.7 | 6 |
| 0.8 | 4 |
| 0.9 | 2 |
| 1.0 | 0 |

When the user is ready to carry out the titration step, container 32 is shaken to thoroughly mix the pH indicator released from ampule 38 and the extractant phase. The user then places the insertion tip 51a of plunger rod 51 into cavity 58c of the plunger head 58 and snaps insertion tip 51a into place. Then, the user removes cap 33 from container 32, breaks off closure tip 53 of titration syringe 50, inserts titration spout 54 into titration container 32, and screws cap 56 into place on the threads 32b of titration container 32. Plunger head 58, as noted above, is positioned within and seals the top (as viewed in FIG. 5) of body 52 of syringe 50. The opening resulting from breaking tip 53 is small enough so that there is no leakage of titration liquid before plunger 51 is operated. With this arrangement, in which cap 56 seals titration container 32, the titration may be performed without the risk of spilling any titration solution or extractant even while gently shaking titration container 32 as titration liquid is added, in order to completely mix the titration liquid with the contents of titration container 32. The user then performs the titration by slowly depressing plunger 51 of titration syringe 50 to expel the basic titration solution from syringe 50 into container 32, while constantly gently shaking container 32. Occurrence of the endpoint is indicated by a color change: in the specific case exemplified, by a color change from magenta to yellow. The resistance offered by the tight fit of plunger head 58 within the body 52 of titration syringe 50 holds the plunger 51 in place at the point where the user stops pushing it to expel the titration solution. This permits the user to easily read the TBN value directly from the graduation 55 printed on body 52 by noting the graduation at the bottom or forward end 58d of plunger head 58. In FIG. 5, plunger 51 is illustrated as being advanced somewhat more than half of its total travel distance. If the titration endpoint occurred at this point, the total base number would be read by the user at the point on the graduations marked by the bottom end 58d of plunger head 58, as indicated by arrow TBN in FIG. 5.

EXAMPLE 1

A commercially successful field test kit in accordance with one embodiment of the present invention is sold under the trademark TITRA-LUBE TBN by Dexsil Corporation of Hamden, Connecticut, the assignee of this application. This kit contains reaction and titration test tube-shaped resilient containers and screw-on caps, a sampling syringe, a filter funnel and a titration syringe substantially as illustrated in FIGS. 1–5A, as well as a small tissue for wiping clean the exterior of the sampling syringe. The kit is packaged in a small cardboard box which includes a hollow box channel formed from heavy paperboard and having a pair of spaced-apart holes formed therein which are dimensioned and configured to receive and hold the test tube-shaped reaction and titration containers in the manner of a test tube rack. This field test kit contains the following components, which are numbered to correspond to the Figures, in addition to the absorbent tissue wipe and other elements illustrated in the Figures. The field test kit contains a sampling syringe 10 of 0.37 ml sample capacity, a reaction container 22 and its closure cap 24, a frangible glass ampule 28 containing 1.0 ml of isooctane, a frangible glass ampule 30 containing 1.0 ml of 0.114N HCl in isopropyl alcohol, a titration container 32 and its closure cap 33, a frangible glass ampule 38 containing 0.2 ml of 1% methyl red in alcohol, seven ml of 1% $Na_2SO_4$ aqueous extractant 42, a filter funnel 48, a sealed titration syringe 50 containing 1 ml of 0.064N NaOH aqueous solution, and a plunger 51 for use as part of titration syringe 50.

A comparable test kit for testing the total acid number of an oil sample would be identical to that described above for testing the total base number, except that instead of hydrochloric acid in an alcohol vehicle it would include a strong base, such as potassium hydroxide, in an alcohol vehicle and the titration liquid would be a suitable acidic species such as an aqueous solution of hydrochloric acid.

The following examples illustrate the efficacy of an apparatus such as that described in Example 1 in determining total base number as compared to laboratory tests carried out on samples of the identical oils tested by use of the illustrated field test kit.

EXAMPLE 2

Part A.

A number of new, i.e., unused, lubricating oils which are commercially available were sampled and tested to determine their total base number both by the American Society for Testing and Materials ("ASTM") Test Standard D2896-88 and by utilizing the field test kit of Example 1.

The laboratory test described in ASTM Standard D2896-88, which is published by the ASTM Committee on Standards, 1916 Race Street, Philadelphia, Pa. 19103, is incorporated by reference herein. This standard test utilizes perchloric acid as the acidic species and dissolves the sample in an essentially anhydrous mixture of chlorobenzene and glacial acetic acid. The sample is titrated with a solution of perchloric acid in glacial acetic acid with a potentiometric titrimeter. A glass indicating electrode and a calomel reference electrode are used, the latter being connected with the sample solution by means of a salt bridge. Meter readings are plotted against the respective volumes of titration solvent, and the endpoint is taken at the inflection in the resulting curve. This ASTM standard provides for both a Procedure A which utilizes 120 ml of titration solvent and a Procedure B which utilizes 60 ml of titration solvent. In carrying out tests of this Example 2, Procedure B was employed as was an Orion Model 960 titrator.

The field test kit in accordance with an embodiment of the present invention was utilized as described above on samples of the same oils tested by the ASTM method. The results given by the ASTM test are given to two decimal places and that by the field test kit to one decimal place in the following TABLE I.

TABLE I

| Lubricating Oil | | TBN Number As Determined By Test Method Of: | |
|---|---|---|---|
| Sample No. | Description | ASTM D2896-88 | Ex. 1 Field Test Kit |
| 1A | Amalie | 12.09 | 12.6 |
| 2A | Quaker State (SAE-30W) | 8.72 | 8.7 |
| 3A | Quaker State HD (20W-20) | 8.08 | 8.2 |
| 4A | Castrol GTX (10W-40) | 7.84 | 7.2 |
| 5A | Castrol Motorcycle | 6.43 | 5.8 |
| 6A | Kendall Super D III | 10.96 | 10.4 |
| 7A | Penzoil Multi High Viscosity (10W-30) | 9.08 | 8.8 |
| 8A | Amoco LDO All Seasons (20W-50) | 8.95 | 8.5 |
| 9A | Mobil 1 (15W-50) | 7.05 | 7.4 |

Part B.

Similar tests were conducted on used lubricating oils and the results obtained by the same two respective test methods are set forth in the following TABLE II. The brand names of the used oils of TABLE II are not known, but these samples comprised used crankcase oils taken from diesel engines operated by a number of different users.

TABLE II

| Lubricating Oil Sample No. | TBN Number As Determined By Test Method Of: | |
|---|---|---|
| | ASTM D2896-88 | Ex. 1 Field Test Kit |
| 1B | 8.17 | 7.2 |
| 2B | 6.93 | 6.6 |
| 3B | 6.48 | 6.2 |
| 4B | 7.24 | 6.5 |
| 5B | 5.45 | 5.9 |
| 6B | 9.29 | 9.0 |
| 7B | 7.39 | 5.7 |
| 8B | 8.37 | 7.5 |
| 9B | 16.10 | 16.4 |
| 10B | 13.40 | 12.8 |

It will be noted from TABLES I and II above that the field test kit in accordance with one embodiment of the present invention uniformly provided TBN results which closely correlated those provided by a sophisticated laboratory procedure. The data of TABLES I and II show that in those cases wherein the difference in TBN determined by the two tests was the greatest (Samples 4A, 5A, 1B, 4B, 7B and 8B) the exemplified field test kit provided a uniformly lower TBN number than that provided by the laboratory analysis, thus providing a safety factor in that it under-reported rather than over-reported the TBN number as compared to the laboratory test. As is well known, because ASTM Test Method D2896-88 uses perchloric acid, a very strong acid, it reacts with even the weakest basic species (which are very poor at neutralizing acidic combustion by-products) present in the sample. The result is that test method D2896-88 over-estimates the usable TBN. For example, ASTM Test Method D4739-87, which employs hydrochloric acid as the acidic species, yields a lower TBN for a given sample than does ASTM D2896-88, by as much as 2 to 3 TBN units on some used oils, and reflects the usable TBN more accurately. Nonetheless, the data show that the results between the two tests are closely comparable, indicating the reliability of the disposable, field test kit which is usable by untrained persons whereas a skilled laboratory technician is required to use relatively sophisticated equipment to carry out the ASTM test. The kit is referred to as "disposable" because it can be manufactured at relatively low cost and may be economically used and discarded after the single use for which it is designed.

While the invention has been described in detail with reference to a specific embodiment thereof, it will be apparent that upon a reading and understanding of the foregoing, numerous alterations to the described embodiment will occur to those skilled in the art and it is intended to include such alterations within the scope of the appended claims. For example, the various stated volumes and concentrations of reagents, i.e., the volume of sample oil, the predetermined quantity of acidic species, the predetermined quantity of extractant mixed with the oil and used for titration may all be varied, as will be appreciated by those skilled in the art, as long as appropriate compensations relating to the concentration of, e.g., the acidic species and the basic solution in the titration syringe, are made. Further, the invention is not limited to the specific acidic species, basic titration solution or pH indicator; these may also be varied within the scope of the present invention by those skilled in the art. Finally, the invention is not limited to the employment of an aqueous extractant phase; other extractants which perform substantially in the same way to achieve the same result may likewise be used.

What is claimed is:

1. A method for determining the quantity of a resident species present in a sample of oil, the method comprising the steps of:
    (a) taking an oil sample of measured quantity;
    (b) contacting the oil sample with an excess quantity of a reactant species which will react with the resident species and reacting the reactant species with resident species, if any, present in the oil sample, thereby consuming a quantity of the reactant species commensurate with the quantity of resident species present in the oil sample;
    (c) after step (b), contacting the oil sample with a fixed quantity of an extractant in which the reactant species is soluble but which is immiscible with the oil sample, to extract any unconsumed reactant species from the oil sample, and then separating the extractant from the oil sample to thereby provide an extractant phase containing reactant species, if any, extracted from the oil sample; and
    (d) measuring the reactant species content of the extractant phase to determine the quantity therein of unreacted reactant species as a measure of the resident species content of the oil sample.

2. The method of claim 1 further comprising solvating the oil sample in a quantity of organic solvent in which the oil sample and any resident species contained therein are soluble, to provide a solvent phase oil sample, and carrying out steps (b) and (c) with the solvent phase oil sample.

3. The method of claim 1 or claim 2 wherein the step of separating the extractant from the oil sample includes removing the extractant from contact with the oil sample.

4. The method of claim 1 or claim 2 wherein the extractant is an aqueous extractant.

5. The method of claim 1 or claim 2 wherein both the resident species and the reactant species are selected from the group consisting of acidic species and basic species, provided that when the resident species is a basic species the reactant species is an acidic species and when the resident species is an acidic species the reactant species is a basic species.

6. The method of claim 5 wherein the resident species is a basic species whereby the content thereof in the oil sample may be expressed as a total base number, and the reactant species is an acidic species.

7. The method of claim 6 wherein step (d) comprises adding a pH indicator to at least a portion of the extractant phase and titrating the extractant phase to the endpoint of the pH indicator using a titration syringe which contains a basic titration liquid and which bears graduations which are scaled and numbered to directly indicate the total base number of the oil sample by the total amount of titration liquid expelled from the titration syringe into the extractant phase upon reaching the endpoint of the titration.

8. The method of claim 6 wherein the acidic species is selected from the class consisting of hydrochloric acid, nitric acid, sulfuric acid and perchloric acid.

9. The method of claim 5 wherein the resident species is an acidic species whereby the content thereof in the oil sample may be expressed as a total acid number, and the reactant species is a basic species.

10. The method of claim 9 wherein step (d) comprises adding a pH indicator to at least a portion of the extractant phase and titrating the extractant phase to the endpoint of the pH indicator using a titration syringe which contains an acidic titration liquid which bears graduations which are scaled and numbered to directly indicate the total acid number of the oil sample by the total amount of titration liquid expelled from the titration syringe into the extractant phase upon reaching the endpoint of the titration.

11. The method of claim 9 wherein the basic species is selected from the class consisting of potassium hydroxide and sodium hydroxide.

12. A method for determining the quantity of resident species present in a sample of oil, wherein the resident species is selected from the group consisting of basic species and acidic species, the method comprising the steps of:
   (a) taking an oil sample of measured quantity;
   (b) contacting the oil sample with a quantity of organic solvent at least sufficient to dissolve therein the oil sample and the resident species, if any, present in the oil sample, to thereby provide a solvent phase;
   (c) contacting the solvent phase with an excess quantity of a reactant species in an alcohol vehicle to react the reactant species with any resident species present in the solvent phase, thereby consuming a quantity of the reactant species commensurate with the quantity of resident species present in the oil sample, the reactant species being (i) an acid when the resident species is a basic species and (ii) a base when the resident species is an acidic species;
   (d) after step (c), contacting the solvent phase with an extractant in which the reactant species is soluble but which extractant is immiscible with the solvent phase, to extract any unconsumed reactant species from the solvent phase, and separating the extractant from the solvent phase, to thereby provide an extractant phase containing reactant species, if any, extracted from the solvent phase; and
   (e) measuring the reactant species content of the extractant phase to determine the quantity therein of unreacted reactant species as a measure of the resident species content of the oil sample.

13. The method of claim 12 wherein the step of separating the extractant from the solvent phase includes removing the extractant from contact with the solvent phase.

14. The method of claim 12 or claim 13 including making a direct determination of the total base number of the oil sample when the resident species is a basic species, or a direct determination of the total acid number of the oil sample when the resident species is an acidic species, wherein step (e) comprises:
   (i) adding a pH indicator to at least a portion of the extractant phase;
   (ii) titrating the extractant phase with a titration liquid contained in a titration syringe bearing graduations to indicate the total volume of titration liquid expelled therefrom, the titration liquid containing a quantity of resident species equivalent which is selected relative to the volume of the oil sample so that the titer indicated by the graduations is the total base number of the oil sample when the resident species is a basic species, as is the total acid number of the oil sample when the resident species is an acidic species, the titration being carried out by expelling the titration liquid into the extractant phase until the pH indicator changes color to indicate the endpoint of the titration, and thereupon ceasing to expel titration liquid from the titration syringe and retaining the remaining titration liquid within the titration syringe; and
   (iii) reading the graduations at the endpoint of the titration to determine the total volume of titration liquid expelled, and thereby the total base number or total acid number of the oil sample.

15. The method of claim 14 wherein removing the extractant from contact with the solvent phase comprises transferring the extractant to a titration container, and wherein the titration syringe comprises a cap member dimensioned and configured to act as a closure which seals the titration container while admitting the titration liquid therein, and a spout for admitting the titration liquid, the spout being directed into the titration container when the cap member is in place as a closure for the titration container, the method further comprising securing the titration syringe to the titration container before performing the titration and shaking the titration container while admitting titration liquid therein.

16. The method of claim 15 wherein the resident species is a basic species, the titration liquid is a basic titration liquid and the titer indicated by the graduations on the syringe is the total base number of the oil sample.

17. The method of claim 15 wherein the resident species is an acidic species, the titration liquid is an acidic titration liquid and the titer indicated by the graduations on the syringe is the total acid number of the oil sample.

* * * * *

UNITED STATES PATENT AND TRADEMARK OFFICE
CERTIFICATE OF CORRECTION

PATENT NO. : 5,366,898
DATED : November 22, 1994
INVENTOR(S) : R.A. Hagstrom et al

It is certified that error appears in the above-indentified patent and that said Letters Patent is hereby corrected as shown below:

In column 20, line 14, replace "as" with --or--.

Signed and Sealed this

Fourteenth Day of November, 1995

Attest:

BRUCE LEHMAN

*Attesting Officer*     Commissioner of Patents and Trademarks